(12) United States Patent
Calignano et al.

(10) Patent No.: US 6,348,498 B1
(45) Date of Patent: Feb. 19, 2002

(54) CONTROL OF PAIN WITH ENDOGENOUS CANNABINOIDS

(75) Inventors: Antonio Calignano; Giovanna La Rana, both of Naples (IT); Andrea Guiffrida, Laguna Beach; Daniele Piomelli, Irvine, both of CA (US)

(73) Assignee: Neurosciences Research Foundation, Inc., San Diego, CA (US)

( * ) Notice: Subject to any disclaimer, the term of this patent is extended or adjusted under 35 U.S.C. 154(b) by 0 days.

(21) Appl. No.: 09/322,843

(22) Filed: May 28, 1999

Related U.S. Application Data

(60) Provisional application No. 60/087,289, filed on May 29, 1998.

(51) Int. Cl.$^7$ ............................................... A61K 31/16

(52) U.S. Cl. ........................ 514/613; 514/627; 514/625

(58) Field of Search ................................ 514/625, 627, 514/613

(56) References Cited

U.S. PATENT DOCUMENTS

| | | | | |
|---|---|---|---|---|
| 5,618,955 A | * | 4/1997 | Mechoulam et al. | .......... 554/66 |
| 5,925,972 A | | 7/1999 | Piomelli et al. | ............ 514/460 |
| 5,990,170 A | * | 11/1999 | Valle et al. | .................. 514/613 |

OTHER PUBLICATIONS

"Behavioral Comparisons of the Stereoisomers of Tetrahydrocannabinols", *Life Sciences*, vol. 29, No. 6, pp. 565–574 (1981).
"International Multidisciplinary Journal Devoted to Fundamental Research in the Brain Sciences", *Brain Research*, vol. 229, No. 2, pp. 300–304 (1993).
"Cannabinoid Receptor Localization in Brain", *Proc. Natl. Acad. Sci. USA*, vol. 87, No. 5, pp. 1932–1936 (1990).
"Immunohistochemical Distribution of Cannabinoid CBI Receptors in the Rat Central Nervous System", *Neuroscience*, vol. 83, No. 2, pp. 393–411 (1998).
"Isolation and Structure of a Brain Constituent that Binds to the Cannabinoid Receptor", *American Assoc. for the Advancement of Science*, vol. 258, pp. 1846–1849 (1992).
"Formation and Inactivation of Endogenous Cannabinoid Anandamide in Central Neurons", *Nature*, vol. 372, No. 6507, pp. 686–691 (1994).
"The Formalin Test: A Quantitative Study of the Analgesic Effects of Morphine, Meperidine and Brain Stem Stimulation in Rats and Cats", *Pain*, vol. 4, pp. 161–174 (1977).
"Subcutaneous Formalin–Induced Activity of Dorsal Horn Neurons in the Rat: Differential Response to an Intrathecal Opiate Administered Pre or Post Formalin", *Pain*, vol. 30, pp. 349–360 (1987).
"The Formalin Test in Mice: Effect of Formalin Concentration", *Pain*, vol. 42, pp. 235–242 (1990).
"The Contribution of Excitatory Amino Acids to Central Sensitization and Persistent Nociception After Formalin–Induced Tissue Injury", *The Journal of Neuroscience*, vol. 19, No. 9, pp. 3665–3670 (1992).
"A Second Endogenous Cannabinoid that Modulates Long–Term Potentiation", *Nature*, vol. 388, pp. 773–778 (1997).
"Molecular Characterization of an Enzyme that Degrades Neuromodulatory Fatty–Acid Amides", *Nature*, vol. 384, pp. 83–87 (1996).
"Functional Role of High–Affinity Anandamide Transport, as Revealed by Selective Inhibition", *Nature*, vol. 277, pp. 1094–1097 (1997).
"Suppression of Noxious Stimulus–Evoked Expression of FOS Protein–Like Immunoreactivity in Rat Spinal Cord by a Selective Cannabinoid Agonist", *Neuroscience*, vol. 70, No. 3, pp. 791–798 (1996).
"Investigation of Brain Sites Mediating Cannabinoid–Induced Antinociception in Rats: Evidence Supporting Periaqueductal Gray Involvement", *The Journal of Pharmacology and Experimental Therapeutics*, vol. 276, No. 2, pp. 585–593 (1996).
"Occurrence and Biosynthesis of Endogenous Cannabinoid Precursor, N–Arachidonoyl Phosphatidylethanolamine, in Rat Brain", *The Journal of Neuroscience*, vol. 17, No. 4, pp. 1226–1242 (1997).
"The N–Acylation–Phosphodiesterase Pathway and Cell Signalling", *Chemistry and Physics of Lipids*, vol. 80, pp. 133–142 (1996).
"A Proposed Autacoid Mechanism Controlling Mastocyte Behaviour", *Agents Actions 39*, Special Conference Issue, pp. C145–C147 (1993).
"N–(2Hydroxyethyl)hexadecanamide is Orally Active in Reducing Edema Formation and Inflammatory Hyperalgesia by Down Modulating Mast Cell Activation", *European Journal of Pharmacology*, vol. 300, pp. 227–236 (1993).
"Mast Cells Express a Peripheral Cannabinoid Receptor with Differential Sensitivity to Anadamide and Palmitoylethanolamide", *Proc. Natl. Acad. Sci. USA*, vol. 992, pp. 3376–3380 (1995).
"Evaluation of Binding in a Transfected Cell Line Expressing a Peripheral Cannabinoid Receptor (CB2): Identification of Cannabinoid Receptor Subtype Selective Ligands", *The Journal of Pharmacology and Experimental Therapeutics*, vol. 278, No. 3, pp. 898–999 (1996).
"Molecular Characterization of a Peripheral Receptor for Cannabinoids", *Nature*, vol. 365, No. 6441 pp. 61–65 (1993).
"SR 141716A, A Cannabinoid Receptor Antagonist, Produces Hyperalgesia in Untreated Mice", *European Journal of Pharmacology*, vol. 319, pp. R3–R4 (1997).

(List continued on next page.)

*Primary Examiner*—Frederick Krass
(74) *Attorney, Agent, or Firm*—McDermott, Will & Emery

(57) ABSTRACT

Novel pharmaceutical therapeutic compositions and methods for using same for the treatment of pain experienced by an individual are provided. The compositions contain at least one member selected from among anandamide and palmitylethanolamide.

10 Claims, 6 Drawing Sheets

OTHER PUBLICATIONS

"SR 141716A, Is An Inverse Agonist at the Human Cannabinoid CB Receptor", *European Journal of Pharmacology*, vol. 334, pp. R1–R2 (1997).

"Anandamide Amidohydrolase Activity in Rat Brain Microsomes", *The Journal of Biological Chemistry*, vol. 270, No. 11, pp. 6030–6035 (1995).

"Isotope Dilution GC/MS Determination of Anandamide and Other Fatty Acylethanolamides in Rat Blood Plasma", *FEBS Letters*, vol. 422, No. 3, pp. 373–376 (1998).

"Mechanisms of Disease: The Control of Pain in Peripheral Tissue by Opioids", *The New England Journal of Medicine*, vol. 332, No. 25, pp. 1685–1690 (1995).

* cited by examiner

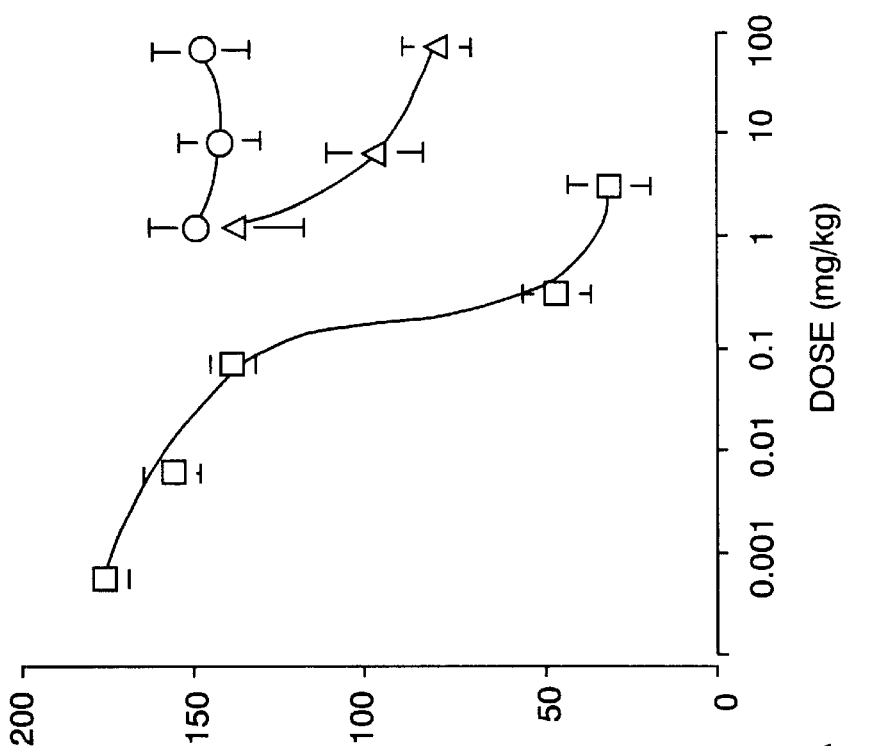
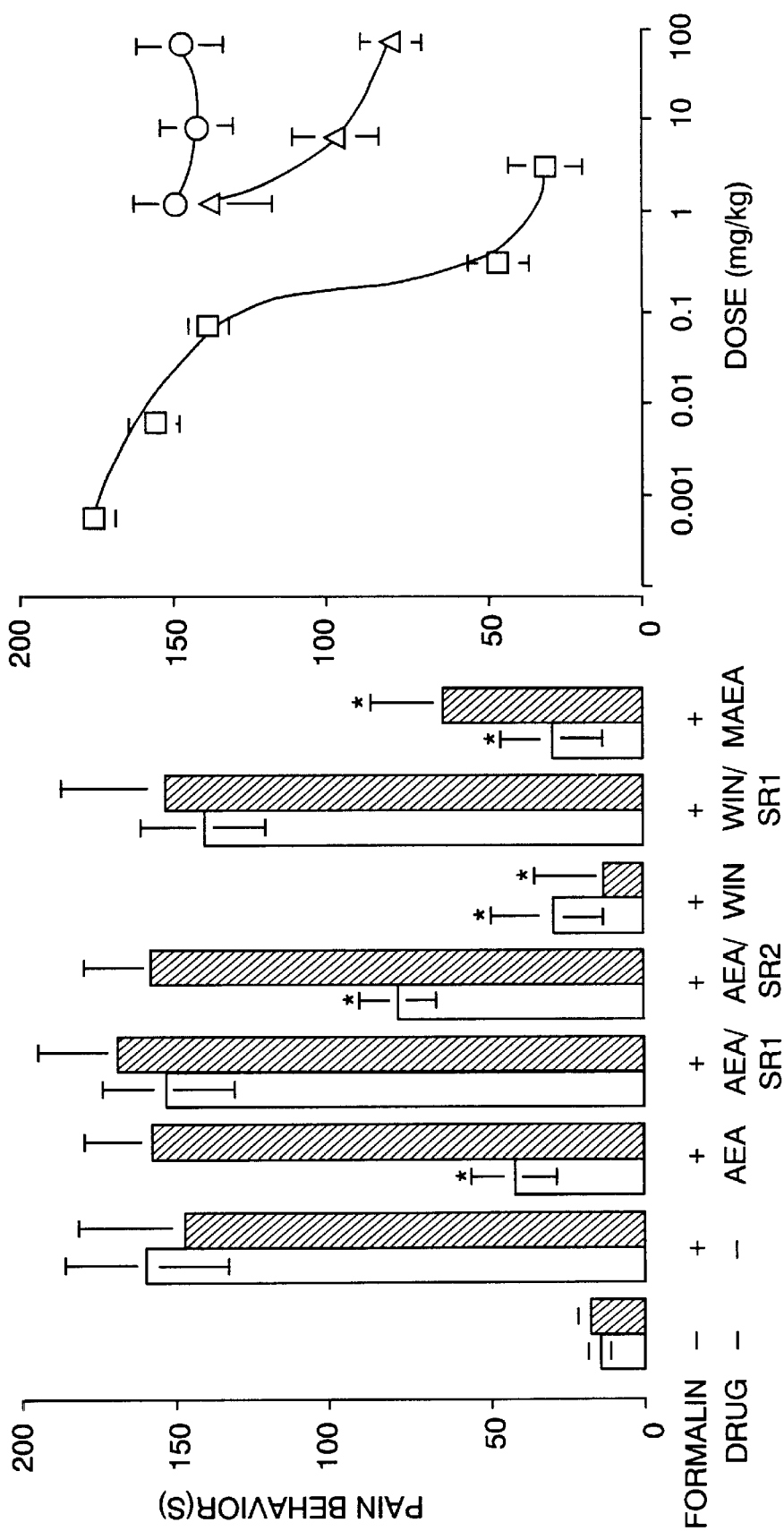

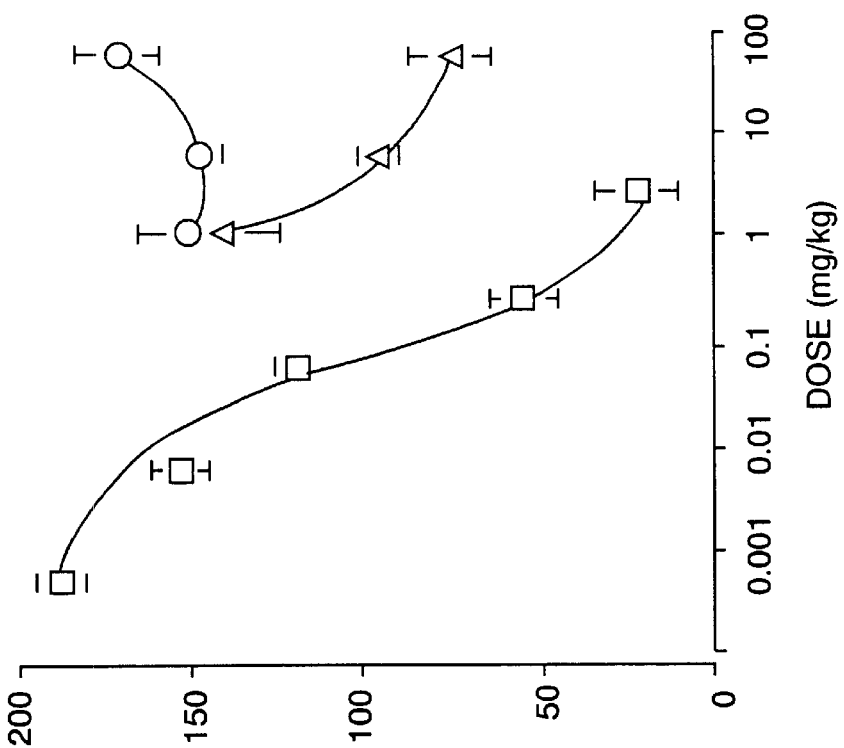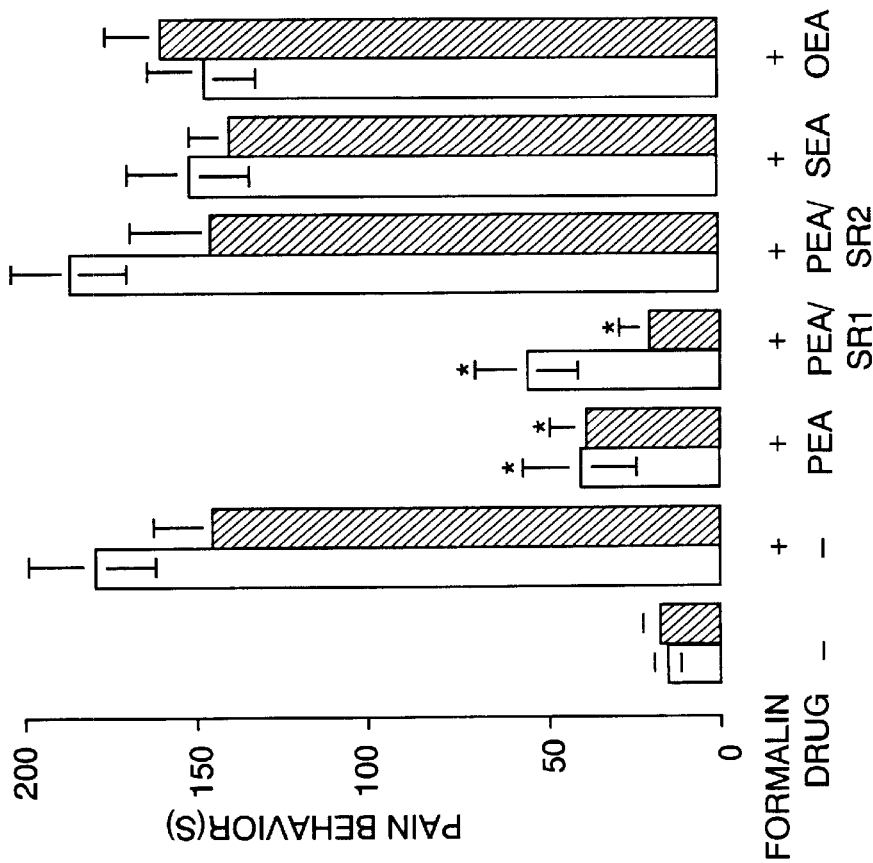

TIME AFTER FOMALIN INJECTION (MIN)

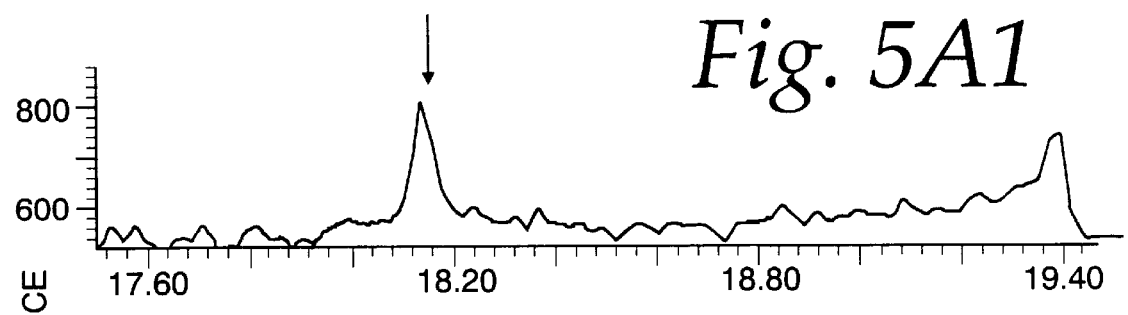
*Fig. 5A1*
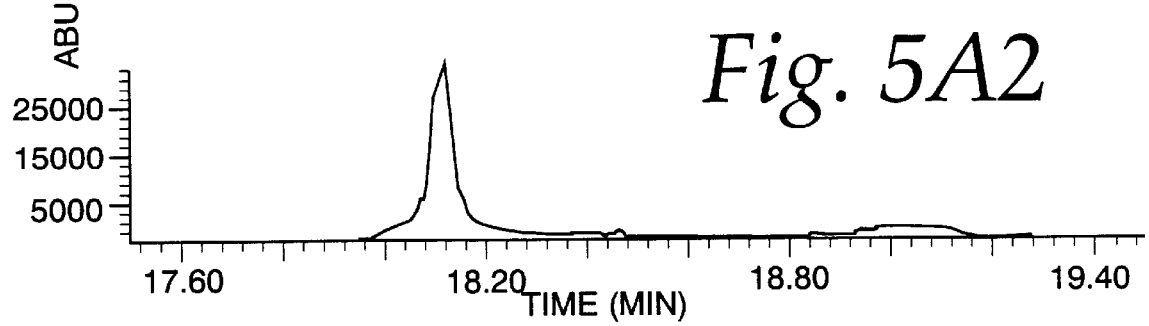
*Fig. 5A2*
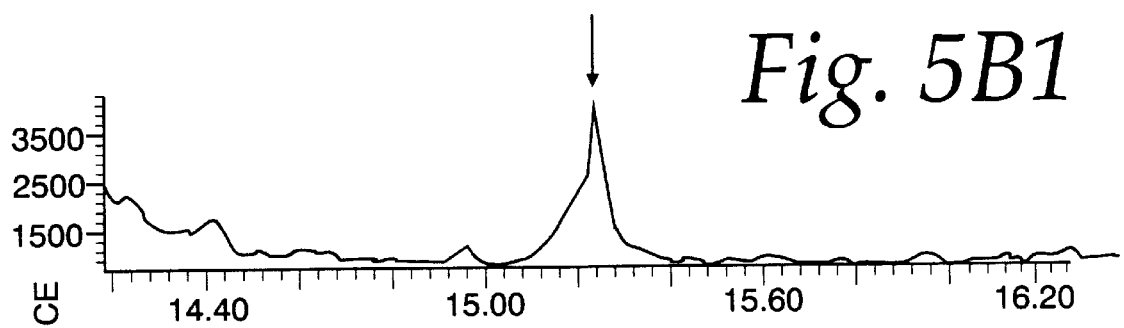
*Fig. 5B1*
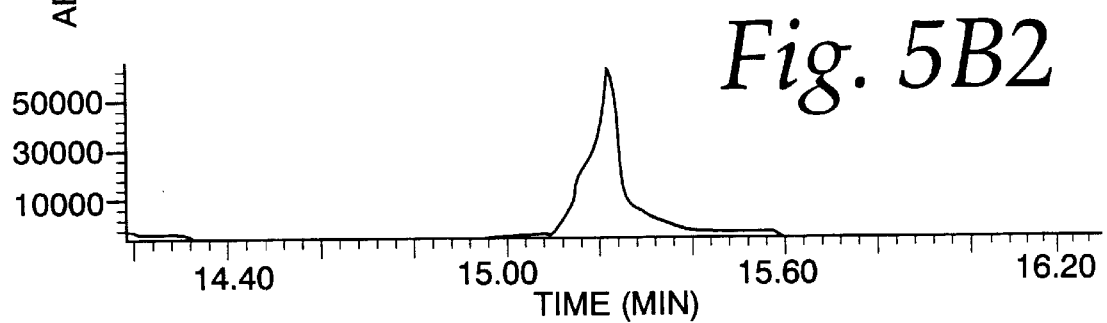
*Fig. 5B2*

CONTROL OF PAIN WITH ENDOGENOUS CANNABINOIDS

This application claims the benefit of U.S. Provisional Application No. 60/087,289, which was filed May 29, 1998, the entire disclosure of which is incorporated herein by reference.

FIELD OF THE INVENTION

The present invention generally relates to novel pharmaceutical compositions for preventing the initiation or transmission of pain signals originating from the peripheral nervous system ("periphery") to the central nervous system of a mammal and methods for using the compositions, alone or in combination with other therapeutic agents, for the treatment and prevention of symptoms or manifestations associated with the sensation of pain caused by a disease or external stimuli. More particularly, the invention relates to methods for controlling pain transmission by administering at a site where the pain transmission originates a therapeutically effective amount of a pharmaceutical composition comprising anandamide alone, palmitylethanolamide alone or a synergistic mixture of anandamide and palmitylethanolamide. When administered together, these two compounds act synergistically reducing pain more potently than each of them alone.

BACKGROUND OF THE INVENTION

Analgesics that can effectively control broad levels of pain with a minimum of side effects are being continually sought. Aspirin, the most commonly used analgesic agent, is of no practical value for the control of severe pain and is known to exhibit undesirable side effects. A number of other analgesics, such as d-propoxyphene, codeine and morphine, possess undesirable side effects, such as addictive liability. It is therefore desirable to have compounds and pharmaceutical compositions having improved and potent analgesic properties without undesirable side effects.

Cannabinoids are compounds that are derived from, or chemically related to, the cannabis sativa plant, which is commonly known as marijuana. The most active chemical compound of the naturally-occurring cannabinoids is tetrahydrocannabinol (THC), particularly $(-)$-$\Delta^9$-THC ("THC"). Many beneficial pharmacological properties attributed to marijuana include analgesia, lowering blood and intra-ocular pressure, and anti-emetic activity in both human and non-human mammals. Indeed, there has been an ongoing debate over whether marijuana use should be legalized in certain cases, e.g., for use by cancer patients for ameliorating the nausea induced by chemotherapy or to lower pain. Since the discovery of THC, several synthetic cannabinoids have been used clinically for the treatment of cancer patients, among these are: Nabilone, Nabortate and Levonantrodol. However, although these drugs are useful, they possess to some extent the negative pharmacologic properties of THC and thus, are limited in their general use. Notable in the negative properties associated with marijuana and cannabinoids include dependency, psychological distortions of perception, loss of short-term memory, loss of motor coordination, sedation, and euphoria. Compounds that exhibit such negative properties or effects have been referred to as cannabimimetics. Throughout the long history of marijuana, its use and abuse have been intertwined.

It is known that the cannabinoids bind to the so-called CB1 and CB2 receptors in the brain and/or other tissues. Compounds that stimulate the CB1 receptor have been shown to induce analgesia and sedation, to cause mood elevation, to control nausea and appetite and to lower intraocular pressure. Thus, compounds or compositions that stimulate the CB1 or CB2 receptor, directly or indirectly, are useful in treating or controlling pain. In addition to acting at the CB1 and CB2 receptors, however, cannabinoids have been shown to affect cellular membranes, thereby producing undesirable side effects such as drowsiness, impairment of monoamine oxidase function and impairment of non-receptor mediated brain function. These addictive and psychotropic properties of cannabinoids limit their therapeutic value.

It would be beneficial to have an alternate mechanism for stimulating CB1 and CB2 receptors in such a way as to eliminate the undesirable addictive and psychotropic properties of cannabinoids. Accordingly, there remains a need for novel therapeutic compositions and methods that inhibit pain without the above adverse effects and without the attendant disadvantages of conventionally available compounds, including cannabinoid compounds.

SUMMARY OF THE INVENTION

It is an object of the present invention to provide novel pharmaceutical compositions and methods useful for inhibiting pain signal initiation and subsequent transmission to the central nervous system in a mammal such that the mammal does not perceive or feel the sensation of pain that it otherwise would have experienced when subjected to pain-causing stimuli.

It is another object of the present invention to provide novel pharmaceutical compositions and methods that are capable of limiting the sensation of pain experienced by a mammal without undesirable side effects.

The above and other objects are accomplished by a pharmaceutical composition comprising a therapeutically effective amount of at least one member of the group consisting of anandamide ("AEA"), palmitylethanolamide ("PEA") and derivatives thereof. Anandamide (arachidonylethanolamide) is thought to be produced by enzymatic cleavage of the phospholipid precursor N-acyl phosphatidylethanolamine (Di Marzo, V., et al., *Nature* 372, 686–691 (1994); Cadas, H., di Tomaso, E. & Piomelli, D., *J. Neurosci.*, 17, 1226–1242 (1997)). Palmitylethanolamide (PEA), which was found in neural and non-neural tissues, has been shown to inhibit mast-cell activation and reduce inflammatory responses (Aloe, L., Leon, A. & Montalcini, R. L., *Agents Actions* 39, C145 (1993); Mazzari, S., Canella, R., Petrelli, L., Marcolongo, G. & Leon, A., *Eur. J. Pharmacol.* 300, 227–236 (1996)) by a mechanism that may involve binding to CB2 receptors (Facci, L., et al., *Proc. Nat'l. Acad. Sci. USA* 92, 3376–3380 (1995); Showalter, V. M., Compton, D. R., Martin, B. R. & Abood, M. E., *J. Pharmacol. Exp. Ther.* 278, 989–999 (1996)).

Anandamide and palmitylethanolamide are readily available compounds that may be obtained via extraction and or purification from sacrificed animals, routine synthesis methods described herein or known in the art or purchased from a suitable commercial supplier. To obtain derivatives, anandamide and palmitylethanolamide may be modified by appending appropriate functionalities to enhance selective biological properties. Such modifications are known in the art and include, without limitation, those that increase penetration into a given biological compartment, increase bioavailability, increase solubility to allow administration by injection, alter metabolism, alter rate of excretion, etc.

In a further aspect, the present invention is directed to a method for treating pain experienced by in a mammal in need of such treatment, the method comprising:

administering to the mammal a therapeutically effective amount of the pharmaceutical composition of the present invention, wherein said composition is capable of inhibiting pain initiation thereby inhibiting or ameliorating pain experienced by the mammal.

The pharmaceutical compositions and methods of the present invention are characterized by their ability to inhibit pain initiation and/or signaling from the peripheral nervous system to the central nervous system. Specifically, the present invention results in the inhibition of pain signaling that induces the sensation of pain felt by a mammal. Without wishing to be bound by theory, it is believed that the pharmaceutical compositions of the present invention short-circuit the intracellular signaling cascade by agonizing CB1- and/or CB2-like receptors found at the periphery of mammals. The present invention regulates pain signaling at the periphery by the activation of local CB1- and CB2-like receptors where it is believed that endogenous cannabinoids participate in filtering and selecting emerging pain signals at sites of tissue injury, a role analogous to that of opioid peptides released from activated immune cells during inflammation. The present invention unexpectedly achieves the above superior and desired effects without the undesired dysphoric side effects and habit-forming properties characteristic of centrally acting cannabimimetic or opiate drugs.

Additional aspects, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

BRIEF DESCRIPTION OF THE DRAWINGS

The accompanying drawings, which are incorporated in and constitute a part of the specification, illustrates embodiments of the present invention and, together with the description, serve to exemplify the principles of the present invention.

FIG. 1 shows that anandamide inhibits the nociceptive response to formalin-evoked tissue damage. (A) Effects of anandamide (AEA, 50 μg intraplantar, i.pl.), WIN-55212-2 (WIN, 500 μg i.pl.) and methanandamide (MAEA, 50 μg i.pl.), in the absence or presence of the CB1 antagonist SR141716A (SR1, 0.1 mg per kg intravenous, i.v.) or the CB2 antagonist SR144528 (SR2, 0.1 mg per kg i.v.). (B) Dose-dependent antinociceptive effects of anandamide following i.pl. (squares), i.v. (triangles) or intraperitoneal (i.p., circles) administrations. *,$P<0.01$ (n=12–18 for each condition).

FIG. 2 demonstrates that palmitylethanolamide inhibits formalin-evoked nociception. (A) Effects of palmitylethanolamide (PEA, 50 μg i.pl.), stearylethanolamide (SEA, 50 μg i.pl.) and oleylethanolamide (OEA, 50 μg i.pl.), in the absence or presence of the CB1 antagonist SR141716A (SR1, 0.1 mg per kg i.v.) or the CB2 antagonist SR144528 (SR2, 0.1 mg per kg i.v.). (B) Dose-dependent antinociceptive effects of palmitylethanolamide following i.pl. (squares), i.v. (triangles) or i.p. (circles) administrations. *, $P<0.01$ (n=12–18).

FIG. 5 shows identification by gas chromatography/mass spectrometry of anandamide and PEA in rat paw skin. (A) Representative tracings for selected fragments characteristic of endogenous anandamide (A1, m/z 404, $[M-15]^+$) and synthetic [$^2H_4$]anandamide (A2, m/z 408) added to the samples as internal standard. (B) Representative tracings for fragments characteristic of endogenous palmitylethanolamide (B1, m/z 356, $[M-15]^+$) and standard [$^2H_4$] palmitylethanolamide (B2, m/z 360). The results are from one experiment, typical of 8.

DETAILED DESCRIPTION OF PREFERRED EMBODIMENTS

Figure 3A:
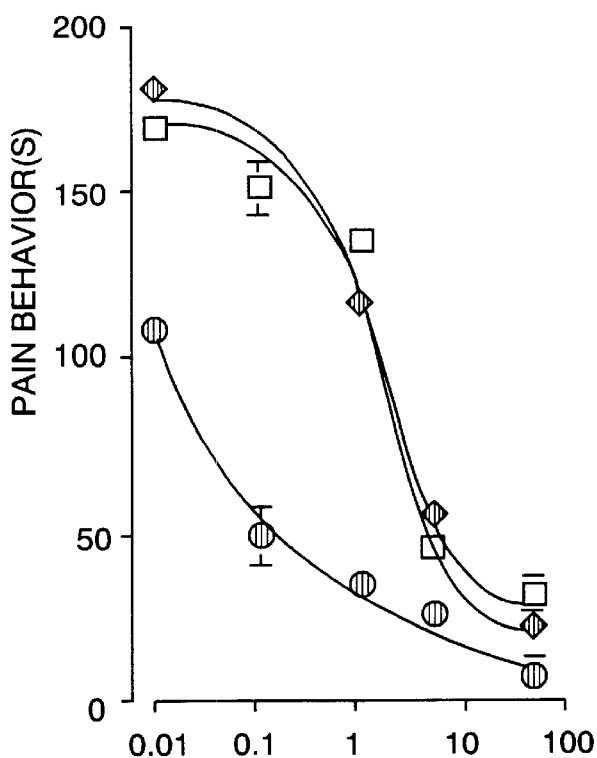
FIG. 3 shows the synergistic antinociceptive effects of anandamide and PEA on (A) early phase and (B) late phase of formalin-evoked pain behavior. Equal amounts of anandamide and PEA, indicated in the abscissa, were injected i.pl. (C) The CB1 antagonist SR141716A (SRI) and the CB2 antagonist SR144528 (SR2) prevent the effects of anandamide plus PEA (0.1 μg each). The antagonists were administered by i.v. injection at the dose of 0.1 mg per kg; *,$P<0.01$ (n=12).

All patents, patent applications and publications cited in this description are incorporated herein by reference in their entirety. In the case of inconsistencies, the present disclosure, including definitions, will prevail.

It is believed that pain transmission in a mammal is the result of a set of receptors collectively acting via a network of intercellular signals or cellular events to initiate the pain signal from an originating site (e.g., site of trauma) at the periphery to the central nervous system (e.g., the brain) where it is perceived or felt by the mammal. In particular, the modulation of pain transmission by cannabimimetic drugs is generally thought to result from the activation of CB1 receptors located in pain-processing areas of the central nervous system, including spinal dorsal horn and periaqueductal gray. Unexpectedly, however, the present invention is based, in part, on the discovery that CB1 or CB2 activation is not accompanied by central signs of cannabinoid intoxication, but rather by a peripheral site of action. Outside of the central nervous system of mammals are cannabinoid or cannabinoid-like receptors at the periphery. Such receptors have shown to be important factors in the biochemical cascade of events that regulate pain felt by an individual.

Throughout this description, the term "treatment" refers to any treatment of pain in a mammal, particularly a human, in accordance with the principles of the present invention and includes, without limitation:

(i) preventing pain experienced by a subject which may be predisposed to the condition but has not yet been diagnosed with the condition and, accordingly, the treatment constitutes prophylactic treatment for the pathologic condition;

(ii) inhibiting pain initiation or a painful condition, i.e., arresting its development;

(iii) relieving pain, i.e., causing regression of pain initiation or a painful condition; or (iv) relieving symptoms resulting from a disease or condition believed to cause pain, e.g., relieving the sensation of pain without addressing the underlying disease or condition.

The terms "pharmaceutically effective" and "therapeutically effective" amount of a composition of the present invention is an amount that results in a sufficiently high level of pain blockage in an individual or animal to cause a physiological effect resulting from the stimulation of cannabinoid or cannabinoid-like receptors. Physiological effects that result from cannabinoid receptor stimulation include without limitation, analgesia. Other physiological functions may also include relieving intraocular pressure in glaucoma patients and suppression of the immune system. Typically, an effective amount of the compound ranges from about 10 mg/day to about 1000 mg/day. A skilled artisan or scientist using routine protocols, such as those disclosed in the Examples below or in the literature, may readily confirm the utility of the compositions described herein.

As used herein, a "mammal" or "individual" refers to humans or animals such as dogs, cats, horses, and the like, and farm animals, such as cows, pigs, guinea pigs and the like.

The present invention is also directed to a method of inhibiting pain initiation or signaling in a mammal having a painful response. The methods of the present invention generally comprise administering a pharmaceutically or therapeutically effective amount of a composition as described herein to a patient in need of such treatment whereby pain signaling is inhibited. The patient may be a human or non-human mammal. For example, a patient will need treatment when exhibiting a painful response in the course of a disease (e.g., rheumatoid arthritis) or traumatic condition. Such need is determinable by skilled clinicians and investigators in the medical arts.

The compositions of the present invention are preferably administered at the site of perceived pain in a topical, subcutaneous or intramuscular form, using dosage forms well known or readily determinable to those of skill in the pharmaceutical arts. The compositions of the present invention can be administered by any means that produces contact of the active agent with the agent's site of action in the body of a mammal, i.e., the site of pain. They can be administered either as individual therapeutic agents or in a combination of therapeutic agents readily determinable by the skilled artisan. They can be administered alone, but are generally administered with a pharmaceutical carrier selected on the basis of the chosen route of administration and standard pharmaceutical practice.

The dosage regimen for the compositions of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the painful condition. Dosage forms (pharmaceutical compositions) suitable for administration may contain from about 1 milligram to about 100 milligrams of active ingredient per dosage unit. In these pharmaceutical compositions the active ingredient will preferably be present in an amount of about 0.5–95% by weight based on the total weight of the composition. Advantageously, compositions of the present invention may be administered in a single daily dose, or the total daily dosage may be administered in divided doses of two, three, four times or more daily, as needed.

The compositions for the present invention can be administered in intranasal form via topical use of suitable intranasal vehicles, or via transdermal routes, using those forms of transdermal skin patches well known to those of skill in that art. To be administered in the form of a transdermal delivery system, the dosage administration will, of course, be continuous rather than intermittent throughout the dosage regimen.

In the methods of the present invention, the inventive compositions can form the active ingredient, and are typically administered in admixture with suitable pharmaceutical diluents, excipients, or carriers (collectively referred to herein as carrier materials) suitably selected. Compositions of the present invention may also be coupled with soluble polymers as targetable drug carriers. Furthermore, the compositions of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Suitable pharmaceutical carriers are described in *Remington's Pharmaceutical Sciences*.

The compositions of the present invention may be administered in combination with a second therapeutic agent such as, for example, a corticosteroid, another analgesic, etc. The compositions of the present invention and such second therapeutic agent can be administered separately or as a physical combination in a single dosage unit, in any dosage form and by various routes of administration, as described above. The compositions of the present invention may be formulated together with the second therapeutic agent in a single dosage unit (that is, combined together in one liquid, etc.). When the compositions of the present invention and the second therapeutic agent are not formulated together in a single dosage unit, they may be administered essentially at the same time, or in any order; for example, the compositions of the present invention may be administered first, followed by administration of the second agent. When not administered at the same time, preferably the administration of a composition of the present invention and the second therapeutic agent occurs less than about one hour apart, more preferably less than about 5 to 30 minutes apart. Although it is preferable that the inventive composition and the second therapeutic agent are both administered by the same route (that is, for example, both subcutaneously or both intramuscularly), if desired, they may each be administered by different routes and in different dosage forms.

The dosage when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of a composition of the present invention when administered in combination with the second therapeutic agent will be readily ascertainable by a medical practitioner skilled in the art, once armed with the present disclosure.

Upon improvement of a patient's condition, a maintenance dose of a composition of the present invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of pain.

Compositions of the present invention can be synthesized using the methods readily available to the skilled artisan, including those methods known in the art of synthetic organic chemistry, or variations thereon as readily appreciated and readily performable by those skilled in the art. Moreover, the synthesis methods known in the art are not intended to comprise a comprehensive list of all means by which the compositions described and claimed in this patent application may be synthesized.

As can be appreciated by the skilled artisan, the specified materials and conditions described below are important in practicing the invention but that unspecified materials and conditions are not excluded so long as they do not prevent the benefits of the invention from being realized. Other suitable methods and starting materials will be evident to those having skill in the art.

EXAMPLES

The present invention will be further illustrated in the following, non-limiting Examples. The Examples are illustrative only and do not limit the claimed invention regarding the materials, conditions, process parameters and the like recited herein. Throughout the examples, unless otherwise noted, inflammatory edemas were produced in the hind paws of Swiss mice by injection of 5% formalin, and were measured with a plethysmometer (Ugo Basile, Italy).

Example 1

Synthesis

Anandamide and PEA, stearylethanolamide and oleylethanolamide were synthesized following standard procedures {N-[(1S)-endo-1,3,3-trimethyl bicyclo [2.2.1]heptan-2-yl]-5-(4-chloro-3-methylphenyl)-1-(4-methylbenzyl)-pyrazole-3-carboxamide} was a generous gift from Sanofi Recherche (Montpellier, France); SR141716A {[N-(piperidin-1-yl)-5-(4-chlorophenyl)-1-(2,4-dichlorophenyl)-4-methyl-1H-pyrazole-3-carboxamide. HCl]} was provided by RBI (Natick, Mass.) as part of the Chemical Synthesis Program of the NIMH (NO1MH30003); all other drugs were from Tocris (Ballwin, Mo.). The drugs were dissolved in dimethylsulphoxide (DMSO), and administered in physiological saline containing 10% DMSO.

Example 2

For instance, injection of dilute formalin in the hind-paws of freely moving rodents evokes a pain behavior consisting of two temporally distinct phases of licking and flexing of the injected limb. An early phase involving activation of primary sensory fibers begins immediately after formalin administration, reaches a peak within 5 min, and rapidly declines. Following an interval of 10–15 min, a second phase of sustained pain behavior appears, in which sensory fiber activity is accompanied by local inflammation and central sensitization.

This Example shows that in mice, the early phase of pain behavior was completely blocked when anandamide was injected in the paw together with formalin, whereas both early and late phase were blocked by the synthetic cannabinoid agonists WIN-55212-2 and HU-210 (FIG. 1A). These antinociceptive effects were reversed by prior systemic administration of the selective CB1 cannabinoid antagonist SR141716A (FIG. 1A), but not of the CB2-preferring antagonist SR144528 (FIG. 1A). The lack of effect of anandamide on late phase pain behavior can be accounted for by the short life-span of this compound, which undergoes rapid biological inactivation in tissues. In keeping with this, the inactivation-resistant anandamide analog methanandamide inhibited pain behavior throughout the testing period (FIG. 1A).

Example 3

FIG. 1B shows measurements during the antinociceptive potency of anandamide following local (intraplantar, i.pl.), intravenous (i.v.) or intraperitoneal (i.p.) administrations. Anandamide was 100 times more potent in preventing formalin-evoked pain behavior when injected i.pl. than i.v., with half-maximal inhibitory doses ($ID_{50}$) of 0.1 mg per kg and 10 mg per kg, respectively (FIG. 1B). Anandamide had no effect when injected i.p. (FIG. 1B).

Example 4

This examples demonstrates the biodistribution of [$^3$H] anandamide 10 min after i.pl. injection in rats. In three experiments, we found that 94% of recovered [$^3$H] anandamide remained associated with the injected paw (6648±820 dpm per g, mean±s.e.m.), whereas little or no radioactivity above background was detected in forebrain, cerebellum and spinal cord (79±19; 165±67; and 90±48 dpm per g, respectively). These results indicate that anandamide inhibits formalin-evoked nociception by activating peripheral CB1-like cannabinoid receptors.

Example 5

This Example shows that PEA, but not two closely related analogs of PEA, inhibited both early and late phase of formalin-evoked pain behavior after i.pl. injection in mice (FIG. 2A). This effect may not be explained by the anti-inflammatory properties of PEA. In six mice, paw volumes were 0.18±0.003 ml under control conditions, 0.37±0.006 ml 30 min after injection of formalin, and 0.35±0.006 ml after injection of formalin plus PEA (50 µg per paw). In addition, the effect of PEA may not result from local anesthetic activity, as the compound did not affect nerve conduction in the rabbit corneal reflex test. PEA-induced analgesia was completely reversed by prior administration of the CB2 antagonist SR144528 (FIG. 2A), whereas the CB1 antagonist SR141716A and the opioid antagonist naloxone were ineffective (FIG. 2A). Like anandamide, PEA was more potent when administered locally (i.pl.) than systemically (i.v. or i.p.) (FIG. 2B). Together, these findings suggest that the antinociceptive activity of PEA is mediated by local CB2-like cannabinoid receptors.

Example 6

Figure 3B:
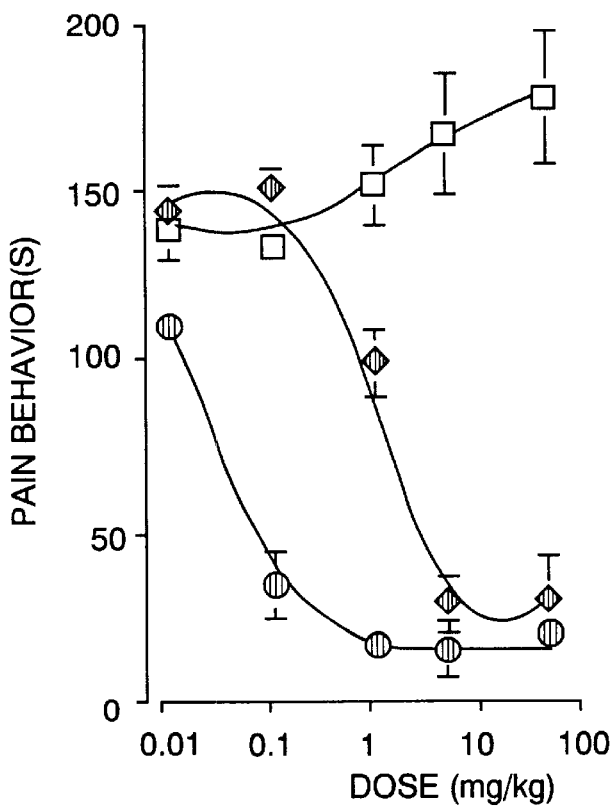
Figure 3C:
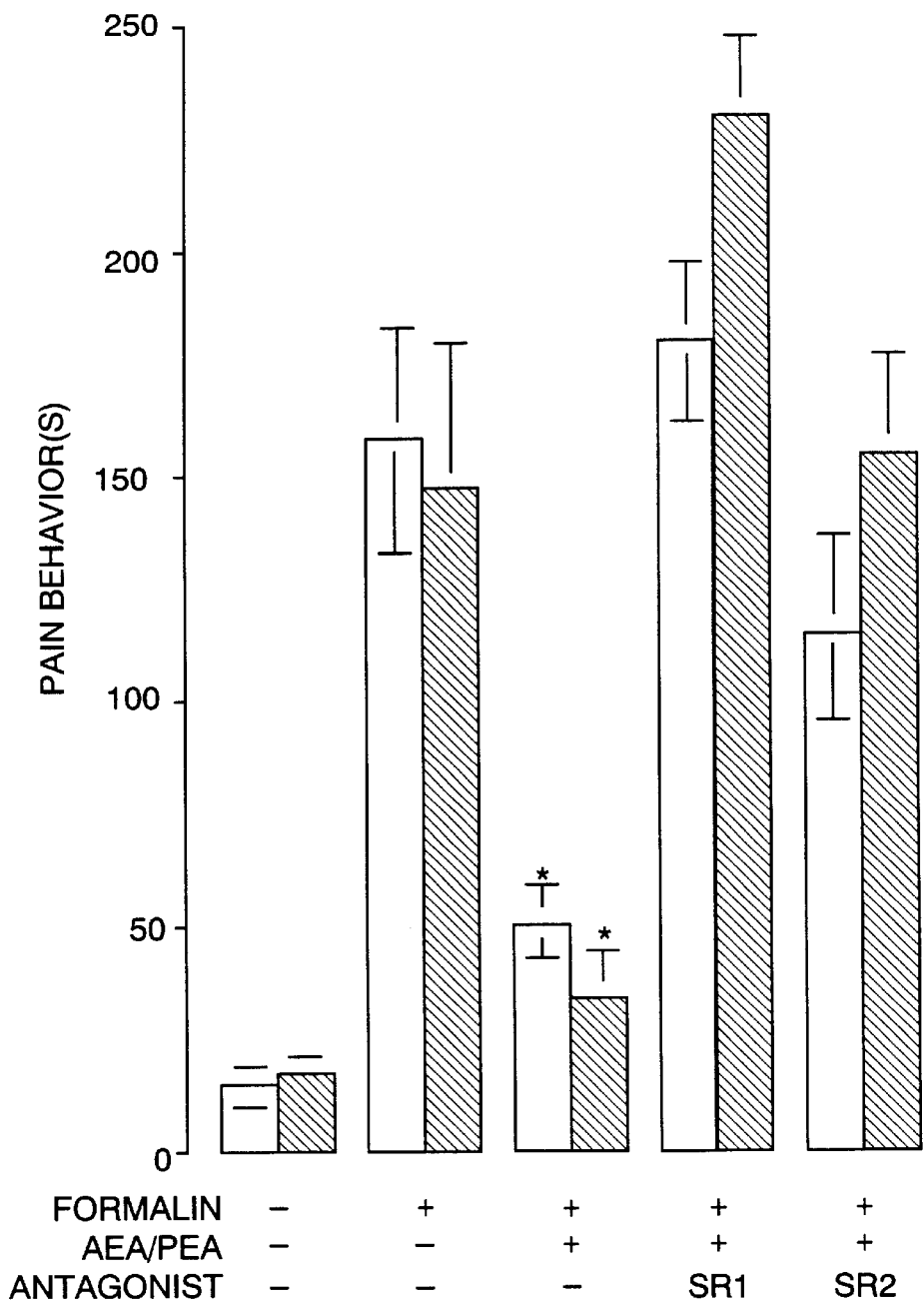

This example shows that when co-injected in equal amounts, anandamide and PEA inhibited the early phase of formalin-evoked pain behavior with a potency that was approximately 100-fold greater than each of the compounds separately (FIG. 3A). A similar potentiation was observed in the late phase, on which anandamide had no effect when given alone (FIGS. 3B and 1A). Prior administration of either CB1 or CB2 antagonists entirely blocked the response (FIG. 3C). This synergistic interaction appeared to be restricted to peripheral antinociception. Indeed, injection of PEA in the cerebral ventricles did not affect the behavioral responses to acute thermal stimuli, assessed in the hot-plate test, and did not enhance the inhibitory activity of anandamide administered by the same route (TABLE 1). Together, these findings suggest that the parallel activation of peripheral CB1- and CB2-like receptors by anandamide and PEA, results in a synergistic inhibition of pain initiation.

TABLE 1

| Time (mm) | vehicle | AEA hot-plate latencies (s) | PEA | AEA/PEA |
|---|---|---|---|---|
| 5 | 24 ± 2 | 24 ± 4 | 22 ± 3 | 25 ± 2 |
| 10 | 24 ± 2 | 23 ± 3 | 23 ± 3 | 26 ± 4 |
| 15 | 22 ± 3 | 29 ± 3 | 21 ± 2 | 30 ± 3 |
| 20 | 25 ± 2 | 35 ± 2* | 25 ± 4 | 37 ± 3* |
| 30 | 25 ± 3 | 40 ± 3* | 26 ± 5 | 39 ± 2* |
| 40 | 25 ± 3 | 30 ± 3 | 22 ± 4 | 35 ± 5 |
| 60 | 26 ± 2 | 28 ± 3 | 24 ± 2 | 26 ± 3 |

Effects of anandamide and PEA on the behavioral response to acute thermal stimuli. Time delays to escape jumping were measured after intracerebraventricular administration of vehicle (10% DMSO in saline, 5 μl), anandamide (AEA, 10 μg), PEA (10 μg) or anandamide plus PEA (10 μg each). *, $P<0.01$ (n=6).

Example 7

Figure 4A:
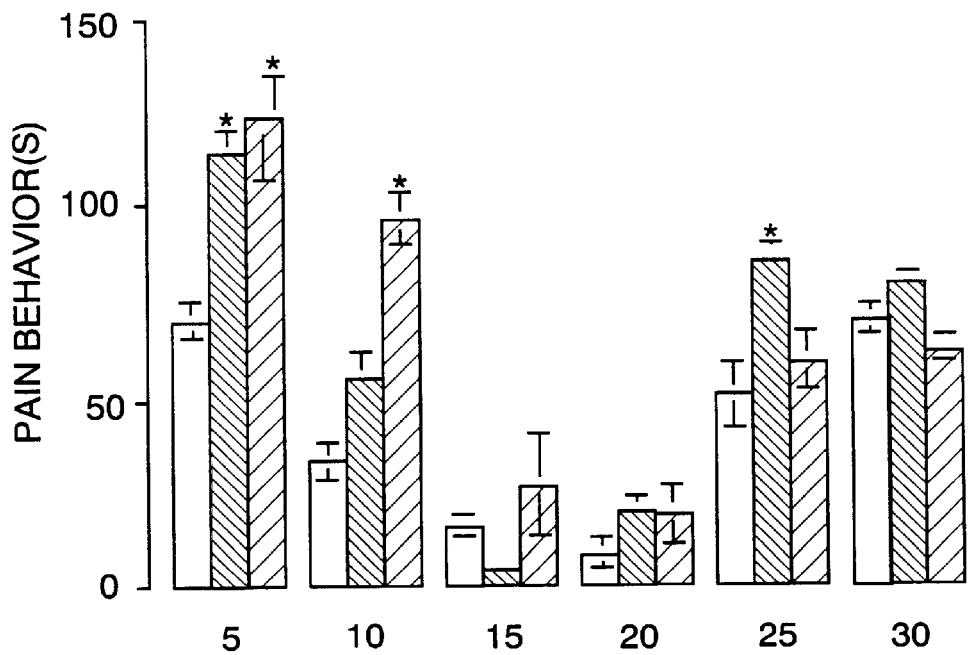
FIG. 4 exhibits intrinsic hyperalgesic effects of cannabinoid antagonists on the time-course of formalin-evoked nociception. (A) Effects of systemic administration of the CB1 antagonist SR141716A (filled bars) and the CB2 antagonist SR144528 (hatched bars). The antagonists were administered by i.v. injection at the dose of 0.1 mg per kg. The responses to formalin alone are shown by the empty bars. (B) Effects of local administration of SR141716A (filled bars). 10 μg of SR141716A were coadministered with formalin by i.pl. injection. SR144528 was not soluble in 10% DMSO, and could not be injected locally. *,$P<0.01$ (n=6).
Figure 4B:
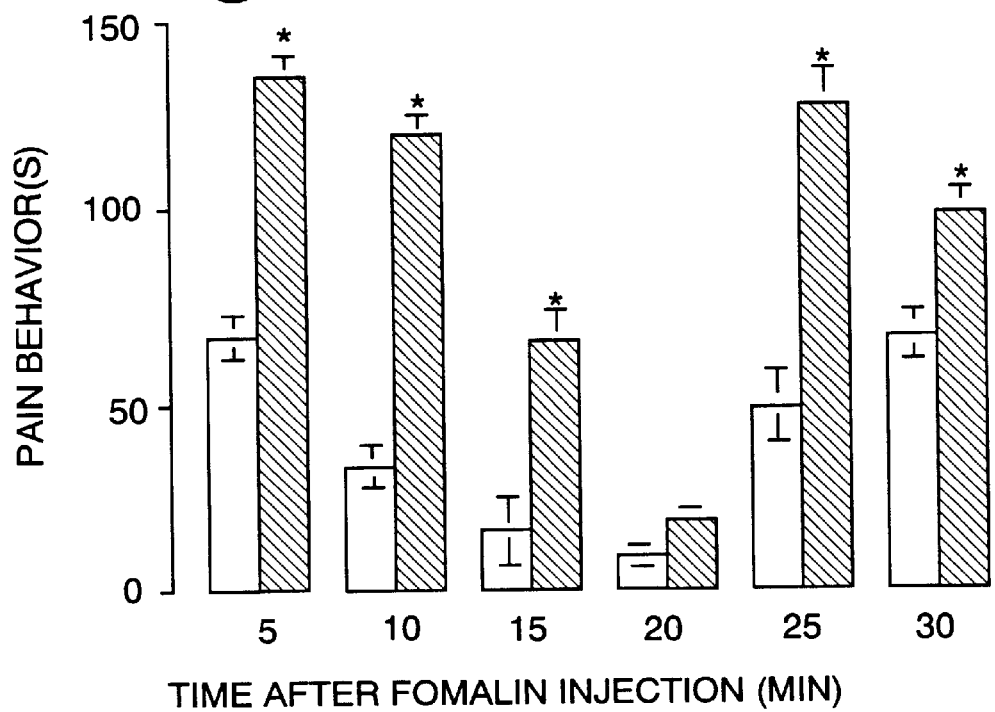

As a further test of this idea, we determined the intrinsic effects of CB1 and CB2 antagonists on formalin-evoked pain behavior. The results of these experiments are illustrated in FIG. 4. A cannabinoid receptor antagonist, produces hyperalgesia in untreated mice. This effect was particularly pronounced after local injection of the drug, which resulted in a 10-min prolongation of the early nociceptive phase and in a 2- to 3-fold increase in pain behavior during the entire testing period (FIG. 4B). By contrast, systemic administration of the CB2 antagonist SR144528 caused a selective enhancement of early phase, but not of late phase behavior (FIG. 4A). SR144528 could not be administered locally because of its limited solubility in the injection vehicle.

Example 8

This Example shows that anandamide and PEA act by removing an endogenous cannabinoid tone. Gas chromatography/mass spectrometry analyses revealed that anandamide and PEA are present in rat paw skin (FIG. 5). By comparison with internal deuterated standards, we measured 49±9 pmol of anandamide and 692±119 pmol of PEA per g of tissue (n=8). These amounts are higher than those measured by the same method in rat brain and plasma (Stella, N., Schweitzer, P. & Piomelli, D. A second endogenous cannabinoid that modulates long-term potentiation. *Nature* 388, 773–778 (1997); Giuffrida, A. & Piomelli D. Isotope dilution GC/MS determination of anandamide and other fatty acylethanolamides in rat blood plasma. *FEBS Lett.* 422, 373–376 (1997)) and are probably sufficient to activate cannabinoid receptors. Furthermore, the CB2 antagonist SR144528 selectively enhanced nociception during the early phase of the formalin response (FIG. 4A), which is incompatible with an inverse agonist effect. This shows that endogenous PEA acting at CB2-like receptors are primarily involved in modulating the early nociceptive phase of formalin-evoked tissue damage, while endogenous anandamide acting at CB1-like receptors exhibit a tonic modulatory action during the entire course of the nociceptive response.

Example 9

Nociceptive Tests

Saline (10 μl) containing 5% formalin and 10% DMSO was injected subcutaneously in the hind-paws of male Swiss mice (20–25 g, Nossan, Italy). The duration of paw licking was monitored by an observer blind to the experimental treatment for periods of 0–15 min (early phase) and 15–30 min (late phase) after formalin administration. For the experiment in FIG. 4, pain behavior was monitored for 5 min periods during a 30 min period following formalin injection. Time delays to escape jumping were measured on a plate heated at 55.5° C., according to standard procedures (Beltramo, M., et al. Functional role of high-affinity anandamide transport, as revealed by selective inhibition. *Science* 277, 1094–1097 (1997)).

Example 10

Anesthesia

Local anaesthetic activity was evaluated in male New Zealand rabbits (2.4–2.8 kg, Morini, Italy) by measuring the number of stimuli to the cornea, delivered with a Frey's horse-hair, necessary to produce the blinking reflex. Aqueous 2% solutions of PEA or lidocaine (a standard local anaesthetic) containing 30% DMSO were applied into the conjuctival sac.

Example 11

Gas Chromatography/Mass Spectrometry (GC/MS)

Paw skin tissue was excised from Wistar rats anesthetized with Nembutal, homogenized and immediately subjected to chloroform/methanol extraction (Cadas, H., di Tomaso, E. & Piomelli D. Occurrence and biosynthesis of endogenous cannabinoid precursor, N-arachidonoyl phosphatidylethanolamine, in rat brain. *J. Neurosci.* 17, 1226–1242 (1997)). Fractionation by high-performance liquid chromatography and quantitative analysis of the trimethylsilyl derivatives of anandamide and PEA by isotope dilution GC/MS were carried out as described elsewhere (Giuffrida, A. & Piomelli, D. Isotope dilution GC/MS determination of anandamide and other fatty acylethanolamides in rat blood plasma. *FEBS Lett.* 422, 373–376 (1997)). Results are expressed as means±s.e.m. The significance of difference between groups was evaluated using ANOVA with a subsequent Dunnett's test.

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A method for treating pain experienced by a mammal in need of such treatment, the method comprising:
   administering to the mammal at a site of perceived pain a therapeutically effective amount of a pharmaceutical composition comprising at least one endogenous cannabinoid selected from the group consisting of anandamide, palmitylethanolamide and mixtures thereof, wherein said pharmaceutical composition is capable of inhibiting pain initiation.

2. The method according to claim 1, wherein the pharmaceutical composition is topically, subcutaneously or intramuscularly administered to the mammal.

3. The method according to claim 1, wherein the pharmaceutical composition comprises anandamide and palmitylethanolamide.

4. The method according to claim 3 wherein anandamide is present in a fifty percent ratio based on the total weight of the endogenous cannabinoid.

5. The method according to claim 3, wherein palmitylethanolamide is present in a fifty percent ratio based on the total weight of the endogenous cannabinoid.

6. A method for controlling pain transmission by administering at a site of perceived pain a therapeutically effective level of a composition comprising anandamide and palmitylethanolamide.

7. The method according to claim 6, wherein the palmitylethanolamide is present in a fifty percent ratio based on the total weight of the composition.

8. The method according to claim 6, wherein the anandamide is present in a fifty percent ratio based on the total weight of the composition.

9. A method for activating peripheral cannabinoid receptors by administering at a site of perceived pain a therapeutically effective amount of a composition wherein said composition comprises anandamide and palmitylethanolamide.

10. The method according to claim 9 wherein the anandamide and palmitylethanolamide are each present in a fifty/fifty ratio.

\* \* \* \* \*